Figure 1:
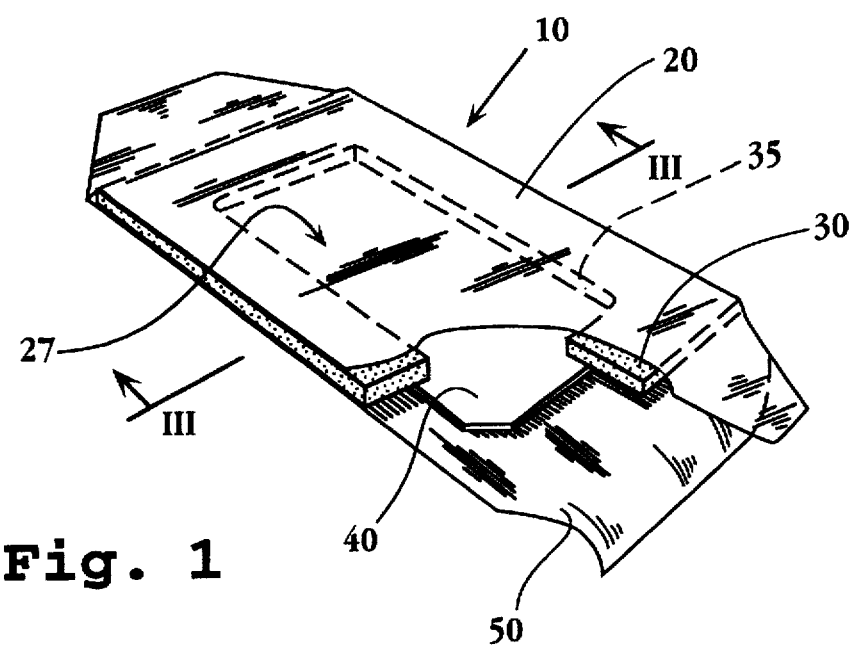

United States Patent [19]
Foldvari

[11] Patent Number: 5,718,914
[45] Date of Patent: Feb. 17, 1998

[54] TOPICAL PATCH FOR LIPOSOMAL DRUG DELIVERY SYSTEM

[75] Inventor: Marianna Foldvari, Saskatoon, Canada

[73] Assignee: PharmaDerm Laboratories Ltd., Saskatchewan, Canada

[21] Appl. No.: 342,962

[22] Filed: Nov. 21, 1994

Related U.S. Application Data

[63] Continuation of Ser. No. 891,594, Jun. 1, 1992, abandoned.

[51] Int. Cl.⁶ .................................................. A61K 9/127
[52] U.S. Cl. ...................... 424/450; 424/449; 604/307
[58] Field of Search .............................. 424/449, 450, 424/443–448; 604/307; 436/829

[56] References Cited

U.S. PATENT DOCUMENTS

| | | | |
|---|---|---|---|
| 4,849,224 | 7/1989 | Chang | 424/434 |
| 4,904,475 | 2/1990 | Gale | 424/449 |
| 4,921,757 | 5/1990 | Wheatley | 428/402.2 |

*Primary Examiner*—Gollamudi S. Kishore
*Attorney, Agent, or Firm*—Judy M. Mohr; Peter J. Dehlinger

[57] ABSTRACT

A device for the dermal and transdermal delivery of liposomes or a formulation thereof. The device comprises an applicator element carrying a containment means to store the liposomes, a liposome delivery surface for the containment means to transfer the liposomes from storage to the skin when the surface is brought into operating proximity therewith and a detachable cover means for the surface. Preferably, the device comprises a screen covering the containment means. The screen is characterized in that it is sufficiently hydrophobic to constitute a barrier for preventing passage of the liposomes when the screen is not in contact with the skin. It also has a plurality of pores of sufficient diameter to allow passage of the liposomes through the screen when the screen is in contact with the skin.

12 Claims, 5 Drawing Sheets

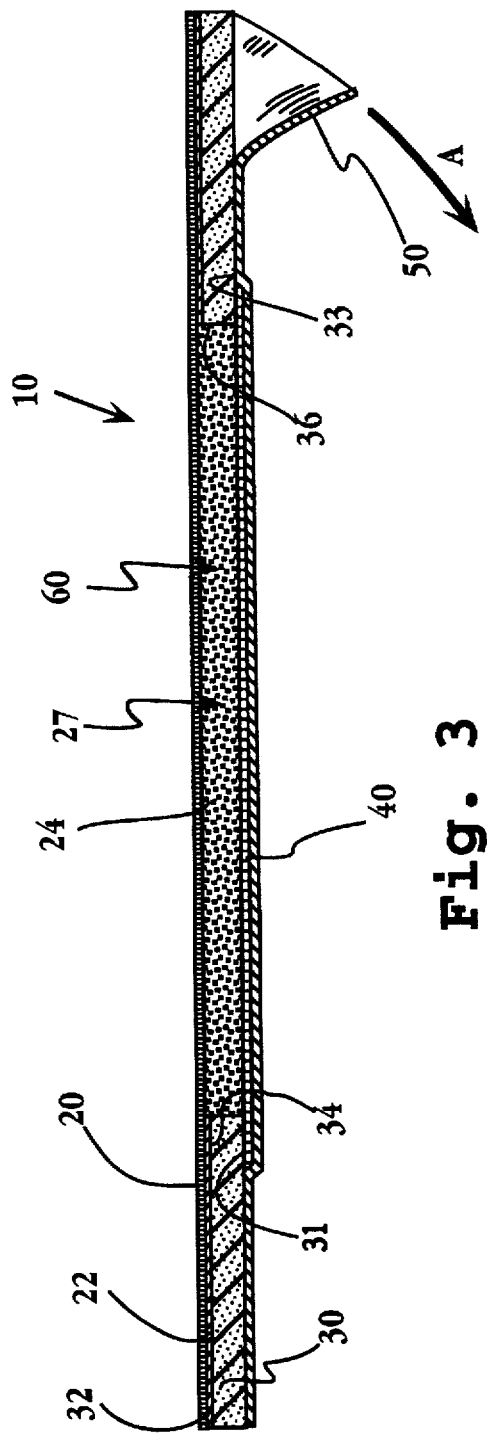
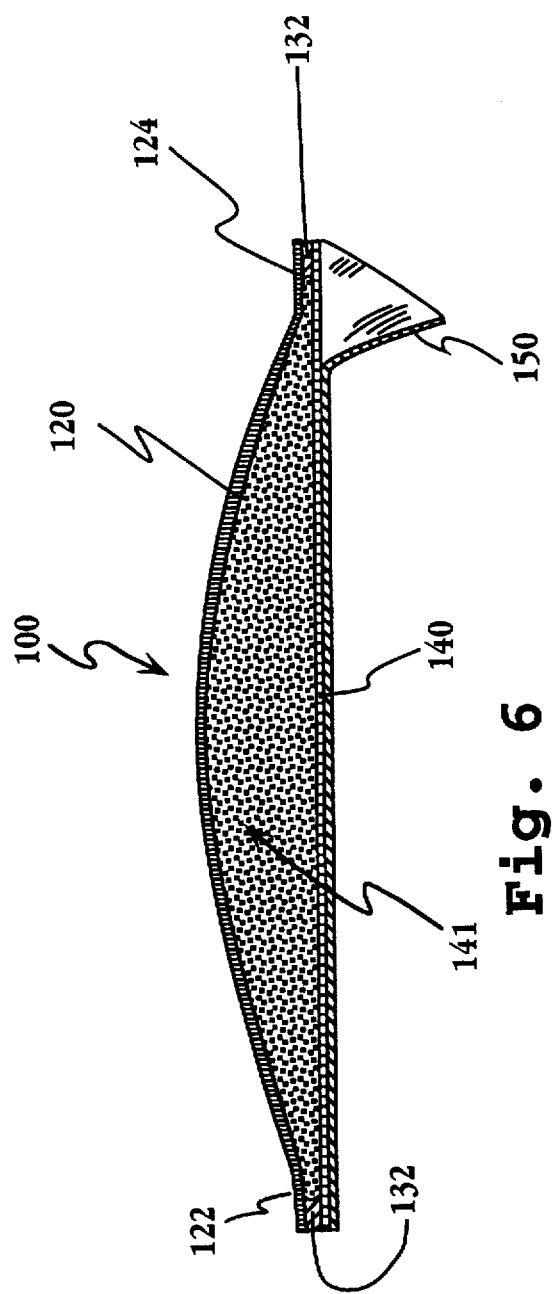

TOPICAL PATCH FOR LIPOSOMAL DRUG DELIVERY SYSTEM

This is a continuation of application Ser. No. 07/891,594, filed on Jun. 1, 1992 now abandoned.

FIELD OF THE INVENTION

The invention relates to devices and methods for the dermal and transdermal delivery of liposomes. The liposomes optionally have encapsulated therein pharmaceutical substances. Particularly, the invention is concerned with the dermal and transdermal delivery of pharmaceutical substances encapsulated in liposomes through controlled partition of the liposomes into the skin or mixing the skin lipids.

BACKGROUND OF THE INVENTION

Drug delivery systems have been the subject of numerous studies in recent years and most efforts have been concentrated on the design of controlled and selective drug delivery systems. In the area of topical delivery, attempts are being made to design new vehicles or utilize drug carriers to ensure adequate skin penetration and more importantly, localization of the drug within the skin. With these attempts, the sophistication of topical delivery systems has markedly increased. The various transdermal therapeutic devices, which contain drugs intended to elicit systemic pharmacologic effects, exemplify a new level of technological involvement.

The ultimate aim of controlled drug delivery is to provide a preprogrammed, unattended delivery at a rate and for a time period to meet specific therapeutic needs. In the case of topical deliveries, there is increasing realisation that a sustained delivery system may be useful for the treatment of various diseases. The mechanisms by which controlled drug input to or through skin tissue may be achieved are basically two-fold: a) the topical vehicle determines delivery, or b) the skin acts as an in-situ rate-controlling membrane metering percutaneous absorption.

A system which is finding increasing acceptance for topical administration of pharmaceutically active agents is one involving liposomes as drug carriers for topical administration. Studies have demonstrated that liposomal encapsulation could favorably alter drug disposition, selectively decreasing drug levels at sites where the drugs would cause adverse effects while concentrating drug levels at the site of action. One of the important aspects of liposomal drug delivery is the fact that the liposomes are readily partitioned into the skin to provide more drug within the epidermis-dermis and significantly decrease the rate of percutaneous absorption. In many instances, percutaneous absorption is undesirable, especially in the case of chronic and extensive treatments as it may lead to unintended systemic and toxic effects of some drugs, such as corticosteroids, salicylates, phenolics and heavy metal-containing agents while, at the same time, not providing a sufficiently high concentration within the skin for a local effect.

Liposomes are microscopic vesicles containing phospholipid bilayers which enclosed aqueous spaces. Multilamellar lipid vesicles or MLV (0.5–20 µm) contain concentric membrane with numerous enclosed aqueous compartments. Large and small unilamellar vesicles (LUV and SUV, respectively) contain one single bilayer and one enclosed aqueous compartment. The structure of the liposome bilayer is similar to cellular membranes. On electron micrographs liposome bilayers show the characteristic "railroad-track" appearance. Similar to the structural arrangement found in living cells, phospholipids are the major components of the lipid bilayer. The phospholipids spontaneously form bilayers and liposomes in aqueous systems because of their amphipathic character. The hydrophobic region, the fatty acid portion, is shielded from the water by facing the inside of the lipid bilayer and the hydrophilic region, the polar head group consisting of phosphoric acid and an alcohol, is immersed in the aqueous environment by facing the outside of the lipid bilayer.

Liposomes were discovered in the 1960s by Bangham (Bangham et al., 1963, Adv. Lipid Res.; 1:65–104). Since then, they were utilized as model membranes to study transport of molecules across bilayers, lipid-protein interactions and physicochemical properties of amphipatic molecules.

Previous reports have indicated potential for liposomes in dermato-pharmacotherapy. In animal experiments the liposomal form, compared to the conventional dosage forms (ointment, cream, gel, lotion), provided higher drug concentration in the intended site of action, i.e. the skin, the lower concentration in the internal organs, i.e. the possible site of adverse or unwanted effects.

The successful application of liposome dispersions on the skin or mucous membranes is highly dependent on the consistency (viscosity) of the preparation. Since liposomes are usually small flexible particles in an aqueous medium (liquid type preparation), they tend to run off the skin when applied, causing frustration in the patient and more importantly decreasing the efficacy of treatment. There are ways to improve the viscosity of the liposome preparations by for example adding viscosity increasing or gelling agents such as cellulose derivatives, carbopol, magnesium aluminum silicate, gelatin, agar, etc. Experiments have shown that these additives usually have a detrimental effect on the availability of the pharmaceutical substance encapsulated in these liposome preparations (drug release is delayed and the amount of drug released per unit time is smaller). The increase of lipid concentration (to 30–35%) can also contribute to the increase in viscosity, however this high amount of lipid increases the cost of the product unreasonably.

Transdermal or transmucosal drug delivery systems have been documented in the patent literature. Such systems are exemplified in U.S. Pat. Nos. 3,598,122, 3,598,123, 3,742, 951, 3,996,934, 4,031,894, 4,201,211, 4,286,592 and 4,379, 454.

However, these systems do not appear to be well-suited for the controlled delivery of liposome encapsulated pharmaceuticals. Hence, in the drug delivery systems described in the prior art, where the pharmaceutical substance is contained in so-called drug-containing microcapsules, these microcapsules remain in the reservoir of the delivery system without contacting the skin. Hence, by using systems of this type, the advantages conferred by the contact of the liposomes with the skin would appear to be lost.

SUMMARY OF THE INVENTION

In accordance with the present invention, there is provided a device for the dermal and transdermal delivery of liposomes or a formulation thereof. The device comprises an applicator element carrying a containment means to store the liposomes. It also comprises a liposome delivery surface of the containment means for the transfer of the liposomes from storage to the skin when the surface is brought into operating proximity with the skin. The device also comprises a detachable cover means for the surface.

The containment means may be a sponge-like element soaked with the liposomes or a formulation thereof. The containment means may also be a reservoir covered with a screen member.

Also in accordance with the present invention, there is provided a device for the dermal and transdermal delivery of liposomes. The device comprises a body having containment means to receive the liposomes. The device also comprises a screen covering the containment means. The screen constitutes means to prevent passage of the liposomes when the screen is not in contact with the skin and it also constitutes means to allow passage of the liposomes through the screen when the screen is in contact with the skin to cause partition of the liposomes into the skin or mixing of the liposomes with skin lipids.

The screen may be conditioned to constitute a barrier for preventing passage of the formulation when it is not in contact with the skin. The screen may be conditioned by having applied thereon or it may be made of a hydrophobic material.

The screen may further be characterized in that it has a plurality of openings or pores for the passage of the liposomes when the screen is in contact with the skin. Liposomes coming in close contact with the skin show sufficient affinity to cross the screen to partition into the skin or mix with skin lipids. Preferably, the pores have a diameter slightly larger than the diameter of the liposomes contained in the patch.

The present invention also relates to a method for the controlled delivery of liposomes on a predetermined surface area of the skin of a mammal. The method comprises providing a screen to cover the predetermined surface area of the skin. The screen is characterized in that it constitutes a barrier for preventing passage of the liposomes when it is not in contact with the skin. It is also characterized in that it has an opening to allow passage of the liposomes through the screen when the screen is in contact with the skin. The method also comprises applying the screen over the predetermined surface area of the skin where the liposomes are to be delivered and applying the liposomes on the screen. Application of the liposomes on the screen causes the liposomes to come in close contact with the skin. The liposomes then have sufficient affinity with the skin to cross the screen and partition into the skin or mix with skin lipids.

Also within the scope of the present invention is a combination for the dermal and transdermal delivery of liposomes. The combination comprises liposomes and a device for the delivery of liposomes. The delivery devices comprises a body having a reservoir adapted to receive the liposomes and a screen covering the cavity and maintaining the liposomes in the reservoir when the screen is not in contact with the skin. The screen has pores of sufficient diameter to allow the liposomes to cross the screen when the screen is in contact with the skin. This causes partition of the liposomes into the skin or mixing of the liposomes with skin lipids.

An important advantage of the device and method of the present invention is the fact that it allows the liposome vesicles to cross the screen and partition into the skin or mix with skin lipids. Experiments have indicated that the liposomes have to be in contact with the skin in order to achieve optimum topical drug delivery. As mentioned previously, if the liposomes are separated from the skin by a limiting membrane, topical delivery is greatly decreased.

Liposomes applied through the device of the present invention had an active principle transfer efficacy that was comparable to that of liposomes directly applied to the skin. This indicates that the device of the present invention does not inhibit contact between the liposomes and the skin. However, when the screen used in the device of the present invention is replaced with a silastic membrane (a non-porous membrane allowing the drug but not the liposomes to penetrate), much lower efficacy was observed.

Another advantage of the device of the present invention when compared to the direct topical application of the liposomal formulation is the convenient localisation of the preparation on a designated area of the skin. At the same time, the device can provide occlusion which enhances the penetration of the liposomes and drug into the skin. It is psychologically more appealing that intradermal injections and is, in many instances, a more humane way of treating animals.

The following is a description by way of example of embodiments of the present invention, reference being made to the accompanying drawings in which:

A BRIEF DESCRIPTION OF THE DRAWINGS

FIG. 1 is a partially cut-away perspective view of a topical liposome delivery patch;

FIG. 2 is an exploded perspective view of the topical liposome delivery patch of FIG. 1;

FIG. 3 is a sectional view taken along lines III—III of FIG. 1;

FIG. 4 is a partial sectional side elevation of the topical delivery patch of FIG. 1 applied on the skin;

FIG. 5 is an enlarged view of a detail of FIG. 4;

FIG. 6 is a side sectional view of an alternative embodiment of a topical liposome delivery patch; and FIG. 7 represents the efficacy of the topical application of tetracaine using various delivery systems.

DETAILED DESCRIPTION OF THE INVENTION

The invention relates to a dermal and transdermal device and method for the topical administration of various types of pharmaceutical or non-pharmaceutical products to humans or mammals through liposomes or liposome formulations. In one of its embodiments, the device of the present invention is a dermal patch comprising a body having receiving means to receive the liposomes and a screen covering the receiving means of the body. The receiving means of the body is generally a cavity which forms a reservoir within which the liposomes or a liposomal formulation are received and stored prior to administration.

Liposomes as microscopic spheres can directly be placed into the reservoir of the patch. Hence, it is possible that the liposomes in this form already constitute the formulation. However, the liposomes can also be an ingredient in a more complex formulation (a cream or ointment which may or may not have a hydrophobic character) and in that case, the final preparation can be filled into the patch cavity.

The screen has a hydrophobic character. The hydrophobic character of the screen can be obtained by having a porous screen made of a hydrophobic material or a porous screen on which a hydrophobic material is applied. The pores of the screen have a diameter slightly larger than the diameter of the liposomes the device or patch carries. Various types of liposome vesicles have been developed and their diameter can vary substantially from one type to another. It is preferred that the diameter of the pore size of the screen be adjusted according to the size of the liposome vesicles so as to have a diameter slightly larger than the size of the liposomes. In most preferred embodiments, the hydrophobic screen has a pore size ranging between 0.1 and 500 micrometers. The size difference between the pore size of the screen and the liposome diameter can influence the rate of liposome release from the patch. The smaller this difference is, the slower the rate of liposome transfer through the screen will be. By using a heterodisperse liposome product, in which liposomes of a wider size range having various diameters can be found, small liposomes can be released at a faster rate than the larger liposomes.

Generally speaking, liposomes are amphipatic vesicles. In other words, they possess both a hydrophilic and a hydrophobic character. Liposomes are usually provided in hydrophilic formulations which are stored into the reservoir of the device or patch of the present invention. The liposome preparation can range from a homogeneous liquid preparation having a texture similar to that of milk to a viscous creamy product. In most cases water, or an aqueous phase, is the external media in which liposomes are embodied. The hydrophilic properties of the outer surface of the liposomes, coupled to the generally hydrophilic character of the formulation, keep the liposomes within the device or patch when the hydrophobic screen is placed over the reservoir but the patch is not used. The screen acts as a repellent to maintain the liposomal formulation within the reservoir.

When it is desired to use the device or patch for topical delivery of a compound, either pharmaceutical or non-pharmaceutical, encapsulated in the liposomes, the screen is brought in contact with the skin of the patient. This causes the liposomes to come in close contact with the skin and allow the liposomes to be in transmitting relationship with the skin. In other words, by being in such close contact with the skin, the liposomes show sufficient affinity for the skin to be transferred from the reservoir through the screen and onto the skin to partition in the skin or to mix with skin lipids. In this situation, the porous screen is not a barrier for either the liposomes or the aqueous phase of the formulation. Hence, in most cases, the liposomes and at least a portion of the formulation pass through the screen when the patch is placed in contact with the skin. In fact, if the formulation is aqueous, its components can be used to hydrate the skin, preparing it for receiving the liposomes. The rate of release of liposomes from the patch can be controlled by regulating the hydrophobicity of the external phase of the liposomes. For example, by increasing the hydrophobic character of the external phase using appropriate solvents or pharmaceutical excipients, it is possible to decrease the rate of release of the liposomes from the patch. Appropriate pharmaceutical excipients include propylene glycol, surfactants, oils, fatty alcohols and the like.

The screen used in the device or patch of the present invention thus has a double-acting function. It first acts to retain the hydrophilic liposomes or liposomal formulation in the containment or reservoir of the patch when the screen is not in contact with the skin. It also allows the liposomes to partition into the skin when brought in contact with the skin.

Hence, when the patch is away from the skin, the hydrophobicity of the screen maintains the pharmaceutical or non-pharmaceutical liposome composition in the cavity. When the patch is approached toward the skin, the affinity of the liposomes for the skin is stronger than the repelling force exerted by the screen which therefore permits the liposomes to cross the screen and partition in the skin.

Figure 2:
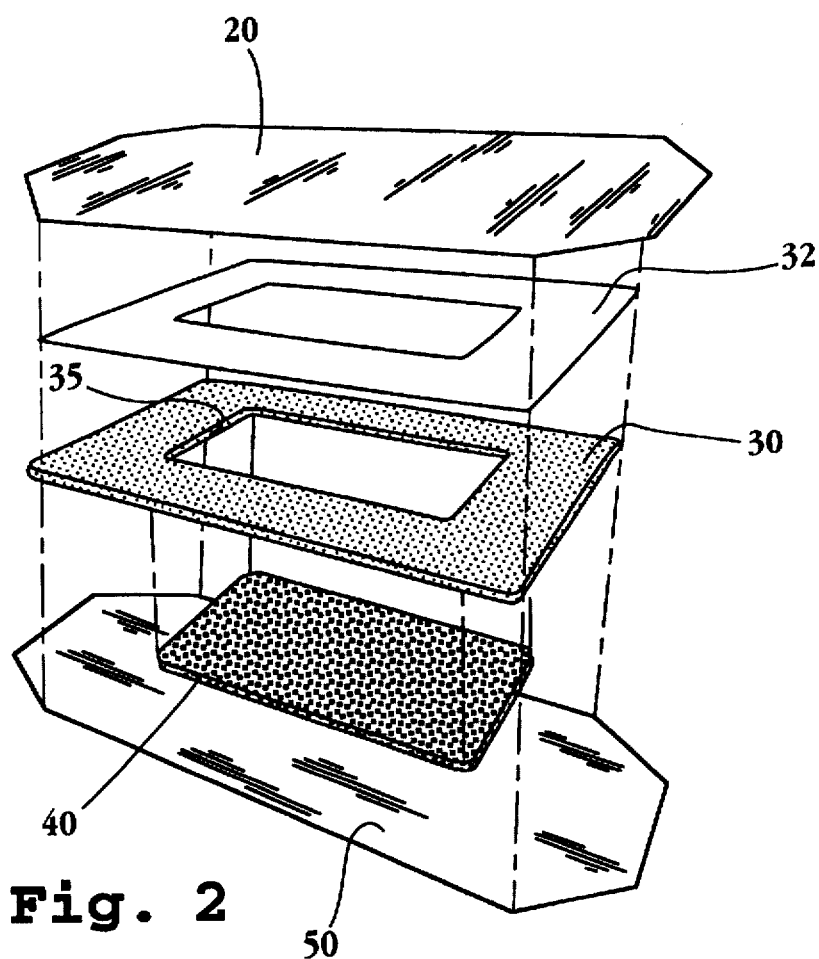

Referring to the drawings and particularly to FIGS. 1 and 2, the patch of the present invention, generally designated by reference numeral 10, has an impermeable backing membrane 20. Backing membrane 20 preferably has a skin tone color for better appearance when the patch 10 is applied to a patient. An impermeable containment member 30 is applied on backing membrane 20 by means of adhesive layer 32 (see FIG. 2). Containment member 30 has a hollow central portion 35 which defines liposome containment means in the form of a liposome reservoir 27 when containment member 30 is applied on backing membrane 20. Hydrophobic screen 40 lies beneath and overlaps the central portion 35 of containment member 30. A cover 50 sandwiches the containment member 30 and hydrophobic screen 40 with impermeable backing membrane 20. Adhesive tabs or adhesive material (not shown) can be applied on the patch 10 to temporarily secure the patch 10 to the skin for the period during which the liposomes are transferred from the patch 10 to the skin.

Referring to FIG. 3 where the patch 10 is shown in further detail, impermeable backing membrane 20 has applied on its inner surface 22 adhesive layer 32 on which is applied containment member 30, preferably of polyethylene foam. A liposome formulation 60 is stored in reservoir 27. It is to be appreciated that the thickness of containment member 30 can be varied to define different volumes for reservoir 27 (FIG. 1).

Hydrophobic screen 40 is applied over containment member 30 to overlap sections 31 and 33 and close reservoir 27. Cover 50, when in the closed position shown in FIG. 3, cover hydrophobic screen 40 and containment member 30. Preferably, a light adhesive (not shown) is applied between containment member 30 and cover 50 to maintain cover 50 in the closed position. Adhesive may or may not be applied on hydrophobic screen 40 but should be avoided.

When it is desired to use the patch 10 to apply liposome formulation 60 to the skin of a patient, cover 50 is pealed off as indicated by arrow A. Hydrophobic screen 40 creates a seal for the containment of liposome formulation 60 in reservoir 27 until the patch 10 is applied to the patient's skin.

Figure 4:
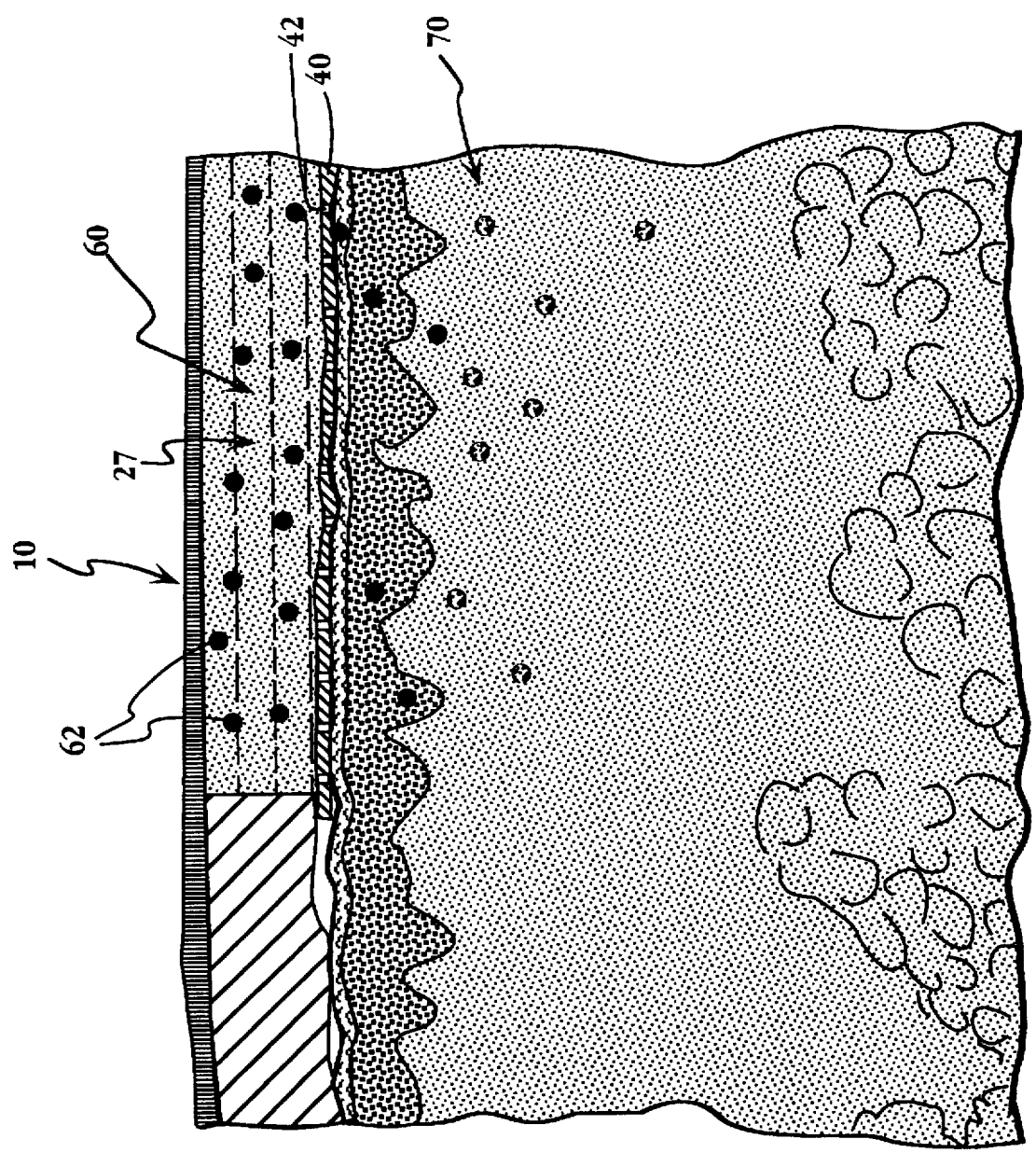
Figure 5:
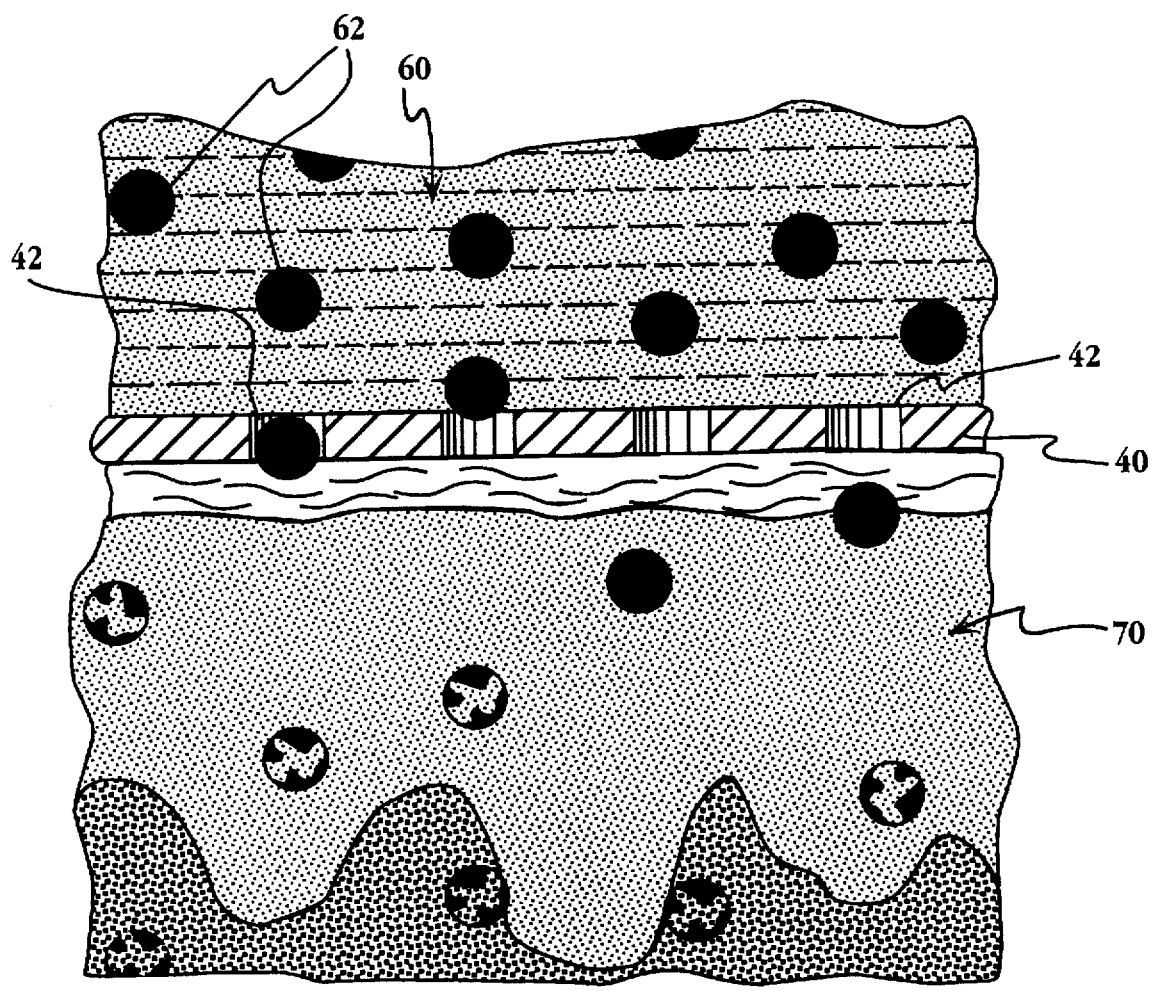

Referring now to FIG. 4, the patch 10 is shown with hydrophobic screen 40 in contact with the skin 70. Upon contact between hydrophobic screen 40 and the skin 70, the screen 40 no longer poses a barrier for liposome formulation 60 contained in reservoir 27, as the liposomes 62 then have sufficient affinity with the skin to cross the screen and partition into the skin or mix with skin lipids. The liposomes 62 contained in the formulation 60 will therefore pass through the openings 42 of the hydrophobic screen 40 and partition into the skin 70. This is shown in further detail in FIG. 5.

Referring to FIG. 5, it can be seen that the diameter of liposomes 62 is slightly smaller than the diameter of pores 42 of hydrophobic screen 40, thereby allowing passage of the liposome formulation 60, including liposomes 62 through pores 42 into the skin 70 when the screen 40 is in contact with the skin.

Hence, the hydrophobic screen 40 does not retain liposomes 62 within the patch 10. When the screen 40 is in contact with the skin, liposomes 62 show sufficient affinity with the skin to pass through the screen 40 and partition into the skin. This is important because contact of the liposomes with the skin is required to benefit from the properties of liposomes as desirable vehicles for increasing the efficiency of topical delivery. The patch of the present invention allows to preserve the original drug release characteristics of liposomes and to ensure contact of liposomes with the desired skin surface area regardless of the consistency of the liposome formulation.

An alternative embodiment of the patch of the present invention is shown in FIG. 6. It can be seen that the patch generally designated by reference numeral 100 has a backing membrane 120 of spherical shape with a hydrophobic membrane 140 adhering to end sections 122 and 124 of backing membrane 120 through adhesive 132, thereby eliminating the need for a member such as containment member 30 shown in FIGS. 1, 2 and 3. The liposome formulation is contained in the cavity 141 formed by the spherical shape of backing membrane 120. Release liner 150 is applied on the surface of hydrophobic screen 140.

In some situations, it may be preferred to have the liposomes in absorbant liposome containment means such as a sponge-like element which can, for example, be placed either in cavity 27 (see FIG. 1) or cavity 41 (see FIG. 6). When the patch is applied to the skin, the sponge is comprised to release its liposome content. In such situations, the skin may act as a regulatory barrier to control the rate at which the liposomes partition into the skin. The use of a sponge is desirable to promote the stability of the liposomes and the patch itself, especially in situations where the patch has to be stored for long periods of time.

In preferred embodiments of the present invention, the impermeable backing membrane is a Scotch pak™ Heat Sealable polyester film (tan color) type 1004, thickness 2.84 made by 3M in St-Paul, Minn. The adhesive layer is Transfer adhesive Type 9871, Pharmaceutical grade, Neutral functional, transparent, ETO radiation tolerant, drug compatible, made by 3M, St-Paul, Minn. The containment member is preferably ARcare 7298 ⅟₁₆", 4 lb. white polyethylene foam with MA-24 medical grade adhesive (supplied on 84# siliconized Kraft paper) made by Adhesives Research, Glen Rock, Pa.

The suitable screens selected for use in the context of the present invention are hydrophobic and have a small pore size (mesh opening 70–100 µm Fluortex™ ETFE monofilament screening square weave fabric or Swiss silk bolting cloth 25 STD (200 mesh count per inch) or PeCap™ polyester monofilament screening square weave fabric (mesh opening 20–100 µm). The hydrophobic screen preferably used in the context of the present invention is manufactured by Schweiz. Seidengazefabrik AG Thal in Switzerland, imported by Tetko™ Inc., Briarcliff Manor N.Y. The cover is preferably a Scotch pak™ Low adhesion polyester film (clear) type 1022, thickness 1.00, made by 3M, St-Paul, Minn.

It is to be understood that the configuration and shape of the device or patch of the present invention can vary widely depending on the area of the skin onto which it is to be applied. The device or patch of the present invention can be used for diversified applications involving topical administration of various compounds, either pharmaceutical or non-pharmaceutical. Examples include the controlled administration of liposomes containing vasodilating agents for the topical treatment of impotence. In this case, the patch can be in the form of an elastic band. Another example is the use of the patch with liposomes containing dyes, bleaching agents and the like to deliver these agents to the skin of humans and animals, (i.e. for tattooing). In this particular instance, the patch can be in the shape of a letter, especially in veterinary applications to indicate the owner of the animal.

The patch of the present invention also finds many uses in the medical field. For instance, it can be used for hospitals or out-patient medical procedures. Examples include the use of a patch for the application of liposomes containing local anaesthetic agents on the skin for relieving the pain of various needling procedures such as lumbar punctures, intramuscular injections, venepunctures, bone marrow or synovial fluid aspirations and intraauricular injections, and minor surgical procedures such as skin biopsies, removal of warts, moles, curettage and electrocautery.

The device of the present invention can also be used in the treatment of various localized skin conditions. Examples include:

a) a patch containing liposomal anaesthetic agents for insect bites and strings or for oral lesions;

b) a patch containing liposomal non-steroidal anti-inflammatory agents such as salicylic acid and podophyllin for warts, corns and calluses;

c) a patch containing liposomal antibacterial agents such as antibiotics for bacterial skin infections such as piodermas furuncles, carbuncles and folliculitis, etc;

d) a patch containing liposomal topical glucocorticosteroids for localized inflammatory skin conditions;

e) a patch containing liposomal anti-cancer drugs for the treatment of precancerous or cancerous lesions of the skin such as keratoses and melanomas;

f) a patch containing liposomal anti-viral agents for the localized treatment of viral skin infections;

g) a patch containing liposomal antihistamines for localized allergic reactions on the skin; and h) a patch containing antifungal agents for localized fungal infections of the skin.

It will be appreciated that even though one of the preferred embodiments of the present invention refers to the use of a hydrophobic screen, there may be some situations (where the liposomes or a formulation thereof is somewhat hydrophobic) in which the polarity of the screen is reversed to be hydrophilic. Furthermore, although the device, as described in the accompanying figures, requires a screen member permitting the passage of the liposomes, it will be understood that there may be some applications in which it is desirable to bring the delivery surface of the containment means, e.g. the face of a sponge, into proximity with the skin in the absence of a screen.

The following example is provided to illustrate rather than limit the scope of the present invention.

EXAMPLE 1

Assessment of the efficacy of various liposome-encapsulated tetracaine formulas in human volunteers.

Methods

In a double-blind design, liposomes containing tetracaine and empty liposomes (placebo) were randomly numbered by a person not participating in the experiments. A single dose of 0.2 g of the above preparations was applied for 15 minutes on premarked 10 $cm^2$ area of the forearm of the volunteers in a random fashion. The liposome preparations were applied either i) directly on the skin and covered with parafilm and Blenderm™ tape (3M Co., St-Paul, Minn.) to provide occlusion, ii) in the patch with the porous screen of FIGS. 1 and 2, iii) in a control patch with a non-porous membrane and iv) liposomes without encapsulated drug were directly applied to the skin as a placebo control. The pin-prick test was used to assess the local anaesthetic effect. The device for the pin-prick test consisted of a surgical pin pushed through a rubber stopper, which prevents the pin from penetrating the skin. This device has been used by anaesthetists for testing of sensory neural blockade during regional anesthesia. The advantage of the device over a needle is more uniform stimulus intensity and prevention of skin injury. Testing was done immediately after removal of the sample and at 15, 30, 45 minutes, and 1, 2, 4, and 6 h.

The topical anaesthetic effect was expressed as mean painful scores out of ten pricks on the skin.

Results

To investigate the applicability of the patch with the porous screen for liposomes in the topical application of drugs tetracaine was chosen since the effect of a local anaesthetic agent on the skin can be assessed fairly easily. The numbness of the skin after application of the liposomes encapsulates tetracaine directly on the skin or in patch form was compared to confirm that the liposomal tetracaine in the patch had similar efficacy than when it was directly applied on the skin.

Figure 7:
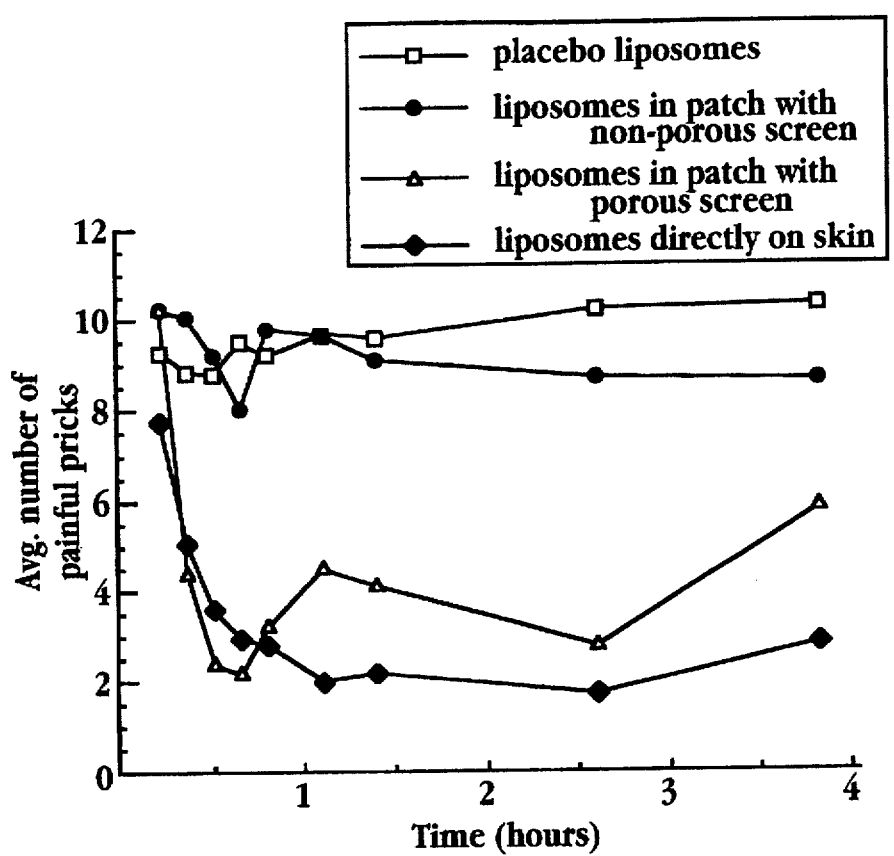

The local anaesthetic effect of liposome encapsulated tetracaine after direct application to the skin or in patch form is shown in Table 1 and in FIG. 7. The results indicate that liposomal tetracaine is equally effective when applied directly onto the skin or in patch form which uses the porous screen. When the preparation is applied through a patch using a membrane which allows the drug but not the liposomes to cross through and penetrate into the skin, no local anaesthetic effect could be detected similarly to the "empty" liposomes (no encapsulated drug). These experiments confirmed that the liposomes have to be in contact with the skin to achieve optimum efficacy and the patch of the present invention is a suitable dermal therapeutic system for liposomes.

2. The device of claim 1, wherein said screen is adhesively attached to said backing.

3. The device of claim 1, wherein said screen is attached to said backing through a member that forms side walls of said reservoir.

4. The device of claim 3, wherein said member is composed of an absorbent foam.

5. The device of claim 4, wherein said member has a central cavity in which said liposomes are contained.

6. The device of claim 1, wherein said compound is an anaesthetic.

7. The device of claim 1, wherein said compound is a non-steroidal anti-inflammatory agent for treatment of a localized skin condition.

8. The device of claim 1, wherein said compound is an anti-bacterial agent for treatment of a bacterial skin condition.

9. The device of claim 1, wherein said compound is a glucocorticosteroid for treatment of localized inflammatory skin conditions.

10. The device of claim 1, wherein said compound is an anti-cancer drug for treatment of precancerous or cancerous lesions of skin.

11. The device of claim 1, wherein said compound is an anti-viral agent for localized treatment of viral skin infections.

12. A topical drug-delivery device, consisting essentially of:

TABLE 1

Efficacy of liposomal tetracaine expressed as the means ± S.D. of the painful pricks on the skin out of ten after 15 min application.

| Testing time | Liposomal tetracaine direct application to skin n = 16 | Liposomal tetracaine in patch with porous screen n = 5 | Liposomal tetracaine in patch with non-porous membrane n = 5 | Empty Liposomes (Placebo) direct application to skin n = 16 |
|---|---|---|---|---|
| immed. after removal. | 7.6 ± 3.5 | 10.0 ± 0 | 10.0 ± 0 | 9.1 ± 1.5 |
| 15 min | 4.9 ± 4.4 | 4.2 ± 3.7 | 9.8 ± 0.4 | 8.6 ± 2.8 |
| 30 min | 3.4 ± 3.3 | 2.2 ± 1.6 | 9.0 ± 1.4 | 8.6 ± 1.8 |
| 45 min | 2.7 ± 2.8 | 2.0 ± 1.9 | 7.8 ± 1.6 | 9.2 ± 0.9 |
| 1 h | 2.6 ± 2.9 | 3.0 ± 2.2 | 9.5 ± 1.0 | 9.0 ± 1.4 |
| 1.5 h | 1.8 ± 2.3 | 4.2 ± 3.7 | 9.4 ± 1.3 | 9.4 ± 0.9 |
| 2 h | 1.9 ± 2.3 | 3.8 ± 2.7 | 8.8 ± 2.2 | 9.3 ± 1.4 |
| 4 h | 1.4 ± 1.9 | 2.4 ± 1.8 | 8.4 ± 3.0 | 9.8 ± 0.5 |
| 6 h | 2.4 ± 2.7 | 5.4 ± 3.8 | 8.2 ± 3.5 | 9.8 ± 0.7 |

I claim:

1. A topical drug-delivery device, consisting essentially of:

a backing, a hydrophobic screen attached to said backing, and forming a fluid reservoir therewith, said screen having pores with a diameter of between 0.1–500 microns, and contained in said reservoir, an aqueous dispersion of liposomes having a compound to be delivered topically, said screen being effective to allow liposomes in the reservoir to pass through the screen out of the reservoir when the device is placed in operative position, with the screen against a subject's skin.

a backing, a hydrophobic screen attached to said backing, and forming a fluid reservoir therewith, said screen having pores with a diameter of between 0.1–500 microns, contained in said reservoir, an aqueous dispersion of liposomes having a compound to be delivered topically, and an adhesive for securing the device to a subjects's skin, wherein said screen is effective to allow liposomes in the reservoir to pass through the screen out of the reservoir when the device is placed in operative position, with the screen against the subject's skin.

* * * * *